(12) United States Patent
Furumoto et al.

(10) Patent No.: US 6,391,022 B1
(45) Date of Patent: *May 21, 2002

(54) ULTRA LONG PULSED DYE LASER DEVICE FOR TREATMENT OF ECTATIC VESSELS AND METHOD THEREFOR

(75) Inventors: Horace W. Furumoto, Wellesley; Harry L. Ceccon, Boston, both of MA (US)

(73) Assignee: Cynosure, Inc., Chelmsford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/007,929

(22) Filed: Jan. 16, 1998

Related U.S. Application Data

(63) Continuation of application No. 08/695,661, filed on Aug. 8, 1996, now Pat. No. 5,746,735, which is a continuation of application No. 08/329,195, filed on Oct. 26, 1994, now abandoned.

(51) Int. Cl.⁷ .............................................. A61B 18/18
(52) U.S. Cl. ................................ 606/9; 606/3; 128/898
(58) Field of Search .............................. 606/2, 3, 9, 18; 607/88, 89; 372/8, 23, 27, 53, 54; 128/898

(56) References Cited

U.S. PATENT DOCUMENTS

| | | |
|---|---|---|
| 4,122,853 A | 10/1978 | Smith |
| 4,293,827 A | 10/1981 | McAllister et al. |

(List continued on next page.)

FOREIGN PATENT DOCUMENTS

| | | |
|---|---|---|
| WO | 91/13652 | 9/1991 |
| WO | 91/13653 | 9/1991 |

OTHER PUBLICATIONS

Anderson, R.R., et al., "Selective Photothermolysis: Precise Microsurgery by Selective Absorption of Pulsed Radiation," *Science*, 220:524–527, Apr. (1983).

Anderson, R.R., et al., "Microvasculature Can Be Selectively Damaged Using Dye Lasers: A Basic Theory and Experimental Evidence in Human Skin," *Lasers in Surgery and Medicine* 1:263–276 (1981).

Anderson, R.R., et al., "The Optics of Human Skin," *The Journal of Investigative Dermatology*, 77(1) :13–19 (1981).

(List continued on next page.)

*Primary Examiner*—Michael Peffley
(74) *Attorney, Agent, or Firm*—Hamilton, Brook, Smith & Reynolds, P.C.

(57) ABSTRACT

A long pulsed dye laser device for selective photothermolysis comprises at least two pulsed dye lasers, such as flash lamp excited dye lasers, each generating corresponding pulsed laser beams successively in time. These laser can be coordinated by a synchronizer that sequentially triggers the lasers. A combining network merges the pulse laser beams into a combined beam and a delivery system conveys the combined pulse laser beam to a patient. An example of a delivery device is a single optical fiber. This invention enables production of the necessary pulse widths, on the order of 2 msec, which can not be achieved by individual dye lasers, generally lower than 0.8 msec. Also disclosed is a selective photothermolysis method. This method comprises irradiating a tissue section of a patient with a pulsed laser beam having a changing color across a time period of the pulse. This pulse color is selected to maximize absorption in a target tissue of a patient in response to heating caused by a preceding portion of the pulse.

1 Claim, 4 Drawing Sheets

U.S. PATENT DOCUMENTS

| | | |
|---|---|---|
| 4,503,854 A | 3/1985 | Jako |
| 4,829,262 A | 5/1989 | Furumoto |
| 4,931,053 A | 6/1990 | L'Esperance |
| 5,009,658 A | 4/1991 | Damgaard-Iversen et al. |
| 5,066,293 A | 11/1991 | Furumoto |
| 5,219,347 A * | 6/1993 | Negus et al. .................. 606/17 |
| 5,287,380 A | 2/1994 | Hsia |
| 5,304,167 A | 4/1994 | Freiberg |
| 5,387,211 A | 2/1995 | Saadatmanesh et al. |
| 5,409,479 A | 4/1995 | Dew et al. |

OTHER PUBLICATIONS

"American Society for Laser Medicine and Surgery Abstracts," *Lasers in Surgery and Medicine*, Supplement 6, p. 46 (1994).

Anderson, R.R., "A Critical Look at Selective Photothermolysis—What is Known, What is Not, and What is Needed," *Plenary Speech at American Society of Laser Surgery and Medicine*, (Apr. 18–20, 1993).

"Selective Photothermolysis—The Candela Vascular Lesion Laser," *Candela*, No Date Given.

* cited by examiner

ULTRA LONG PULSED DYE LASER DEVICE FOR TREATMENT OF ECTATIC VESSELS AND METHOD THEREFOR

RELATED APPLICATION

This application is a Continuation of U.S. Ser. No. 08/695,661, filed Aug. 8, 1996, now U.S. Pat. No. 5,746,735 which is a File-Wrapper-Continuation of Ser. No. 08/329,195, filed Oct. 26, 1994, now abandoned, the entire teachings of which are incorporated herein by reference.

BACKGROUND OF THE INVENTION

Vascular lesions comprising enlarged or ectatic blood vessels have been successfully treated with lasers for many years. In the process, called selective photothermolysis (SP), the lesion is irradiated with laser light. The wavelength or color of the laser light is chosen so that its energy is preferentially absorbed into the lesion, the target tissue. Most commonly in the context of vascular lesions, such as portwine stains for example, hemoglobin of red blood cells within the ectatic blood vessels serves as the chromophore. Ideally, these cells absorb the energy of the laser light and transfer this energy to the surrounding vessels as heat. If this occurs quickly and with enough energy, the surrounding vessels reach a temperature to denature their proteins, which leads to their ultimate destruction. The fluence to reach the denaturation of the vessels is calculated to be that necessary to raise the temperature of the targeted volume within the vessel to about 70° C. before a significant portion of the absorbed laser energy can diffuse out of the vessel.

Flash lamp excited dye lasers meet the wavelength constraints required for selectivity. These lasers are readily tunable to generate pulsed laser light in a range around 580 nm. The greatest disparities between the absorption of hemoglobin and melanin, the principle pigment in the skin, exist in this range.

Wavelength aside, the intensity and pulse width of the laser light must also be optimized in order to maximize selectivity. Proper pulse duration and intensity are important to attain temperatures necessary to denature the vessel's protein without heating too quickly the red blood cells. Boiling and vaporization are desirably avoided since they lead to mechanical, rather than chemical, damage, which can increase injury and hemorrhage in tissue surrounding the lesion. These constraints suggest that the pulse duration should be longer with a correspondingly lower intensity to avoid vaporization. Because of thermal diffusivity, energy from the laser light pulse must be deposited quickly, however, to minimize heat dissipation into the surrounding tissue. The situation becomes more complex if the chromophore is the blood cell hemoglobin within the lesion blood vessels, since the vessels are an order of magnitude larger than the blood cells. Radiation must be added at low intensities so as to not vaporize the small cells, yet long enough to heat the blood vessels by thermal diffusion to the point of denaturation and then terminated before tissue surrounding the blood vessels is damaged.

Theory suggests that the length of the laser light pulse should be on the order of milliseconds, especially for adult patents having characteristically thicker and larger blood vessels. Commercially available dye lasers, however, are generally limited in the pulse durations to approximately 0.5 msec.

A number of attempts have been made to increase the pulse length of dye lasers. One approach is disclosed in U.S. Pat. No. 4,829,262 granted to one of the present inventors. This invention was directed to overcoming thermal distortion in the lasing medium, which leads to loss of the resonating modes. Special resonator optics were proposed that would be less sensitive to opto-acoustic perturbations. Other attempts to increase pulse length have been made by implementing planar waveguide lasers. See Burlmacchi, et al., "High Energy Planar Self Guiding Dye Laser," *Optics Communication*, 11(109) (1974).

SUMMARY OF THE INVENTION

Recent research suggests that special resonators do not prolong pulse duration longer than standard resonator designs. This realization leads to the conclusion that there must be another reason for the quenching of the lasing action than thermal distortion. Subsequent studies on long pulse flash lamp excited dye lasers show that it is nearly impossible to extract pulses from a flash lamp excited dye laser more than one millisecond long and still meet the energy requirements of an output greater than one hundred millijoules needed for SP.

It seems that induced absorption could be a factor in quenching the lasing action. Although transient absorption can be induced, the largest contribution is considered to be permanent transformation in the dye to a light absorbing specie. The dye concentration is set for uniform absorption of pump light across the short dimension of the dye cell, approximately 4 mm. The concentration optimizes at about $7 \times 10^{-5}$ M of dye solution. Meanwhile, the laser length is 600 mm or 150 times longer than the dye cell diameter. A 1/e transmission loss along the gain length would overcome any gain in the laser. The concentration of absorbing specie need only be minuscule, on the order of $3 \times 10^{-7}$ M to stop any gain. This small concentration of absorbers can be readily generated during the excitation pulse.

In light of the fact that research seems to establish that a dye laser can not produce the necessary pulse widths, the present invention is based upon the recognition that the required pulse widths could be achieved by implementing multiple dye lasers and time multiplexing their output beams. For example, if the required pulse width is on the order of two msec, the pulse laser beams from two lasers, each being approximately 0.8 msec long could be multiplexed in time and combined to effectively meet this width specification.

Moreover, the implementation of time multiplexed multicolored pulse laser beams allows the dynamic tracking of the absorption spectra of the chromophore, hemoglobin for example, as it is heated. With temporal multiplexing, lasers of different colors can be used to optimize the selectivity in response to the predicted temperature of the target tissue.

As a result, in general according to one aspect, the invention features a long pulsed laser device for selective photothermolysis. This device comprises at least two pulsed lasers, generating successive laser pulses. The laser can be coordinated by a synchronizer that sequentially triggers the laser. A combining network merges the pulse laser beams into a combined bean and a delivery system conveys the combined laser beam to a patient. Such a combined beam may have an energy of 100 millijoules and a pulse duration from 1 to 10 msec.

In general, according to another aspect, the invention features a method for generating a long effective laser pulse for a selective photothermolysis therapy. This method comprises successively triggering at least two pulse lasers to generate pulsed laser beams. These beams are then combined into a combined beam having all effective pulse width equal to a combination of the pulsed laser beams. Finally, the combined beam is delivered to a patient thought a delivery system.

In general, according to another aspect, the invention features a selective photothermolysis method. This method comprises irradiating a tissue section of a patient with a pulsed laser beam having a changing color across a time period of the pulse. This color is selected to maximize absorption in a target tissue of a patient in response to heating caused by a preceding portion of the pulse.

The above and other features of the invention including various novel details of construction and combinations of parts, and other advantages, will now be more particularly described with reference to the accompanying drawings and pointed out in the claims. It will be understood that the particular method and device embodying the invention is shown by way of illustration and not as a limitation of the invention. The principles and features of this invention may be employed and various and numerous embodiments without the departing from the scope of the invention.

BRIEF DESCRIPTION OF THE DRAWINGS

In the accompanying drawings, like reference characters refer to the same parts throughout the different views. The drawings are not necessarily to scale. Emphasis is instead placed upon illustrating the principles of the invention. Of the drawings.

DETAILED DESCRIPTION OF THE DRAWINGS

Figure 1:
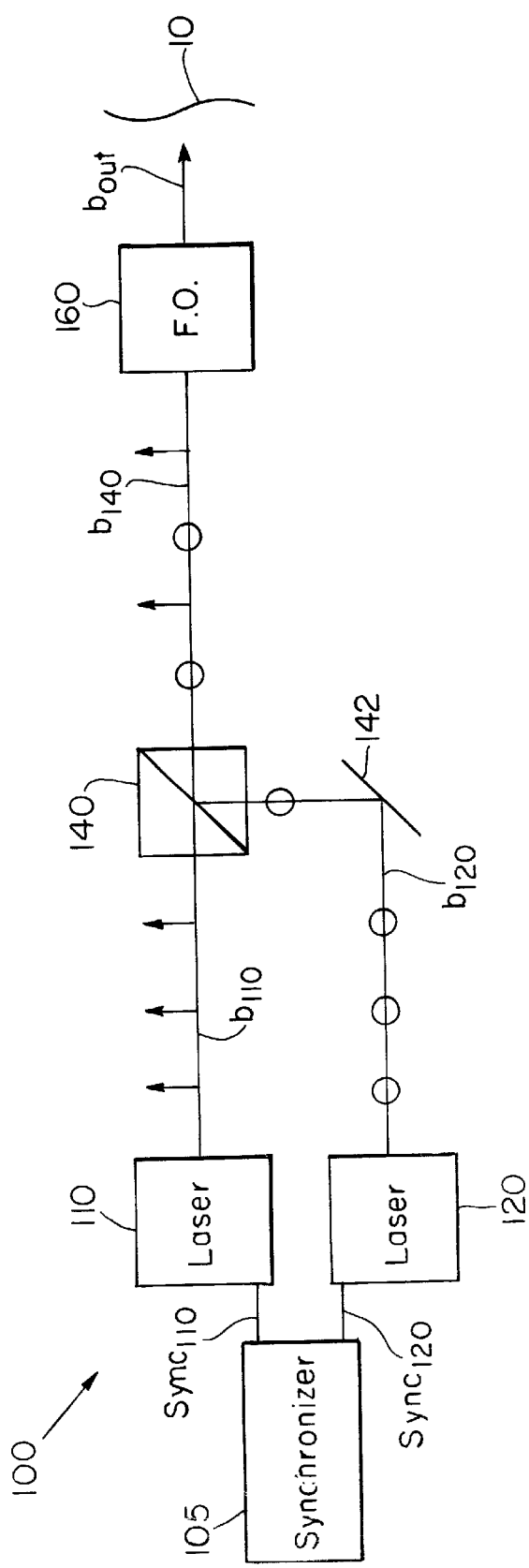
FIG. 1 is a schematic view of a first embodiment of an ultra-long pulsed dye laser device of the present invention.

Turning now to the drawings, a first embodiment 100 of a dye laser device, constructed according to the principles of the present invention, is illustrated in FIG. 1. Generally, two pulse lasers 110, 120 are commonly controlled to generate two pulsed laser beams $b_{110}$, $b_{120}$, one being delayed in time with respect to the other. These beams are then merged into a single beam $b_{140}$ by a combining network, see 140, 142. This merged beam $b_{140}$ is conveyed to a targeted region of the patient, such as that containing a cutaneous portwine stain, by a delivery system, see 160.

In more detail, a synchronizer 105 generates two trigger signals $Sync_{110}$, $Sync_{120}$, with $Sync_{120}$ being delayed in time by approximately 1.3 msec with respect to $Sync_{110}$. In response to their corresponding trigger signals, the lasers 110, 120 generate pulsed laser beams $b_{110}$, $b_{120}$. In the preferred embodiment, the lasers are long pulse flashlamp excited dye lasers.

Pulse laser beam $b_{120}$ is redirected by a fold mirror 142 to spatially converge with beam $b_{110}$ at a polarizer 140. The pulsed laser beams $b_{110}$, $b_{120}$ are generated by their corresponding lasers 110, 120 to have orthogonal polarizations with respect to each other. This can be achieved by filtration at the output of the lasers 110, 120 using orthogonally oriented polarizing filters or by appropriate design of the lasers' resonant cavities. The polarizer 140 is designed and configured such that it permits the transmission of light having the polarization of beam $b_{110}$ but reflects light having a polarization of beam $b_{120}$. As a result, the pulsed laser beams are combined by the combining network 140, 142 into merged beam $b_{140}$.

This merged beam is then coupled into a single optical fiber 160 serving as the preferred delivery system. Alternatively, a fiber optic bundle may be used. Beam $b_{140}$ appears as an output beam $b_{out}$ from the fiber 160 and is applied to the tissue 10 of a patient.

Figure 2:
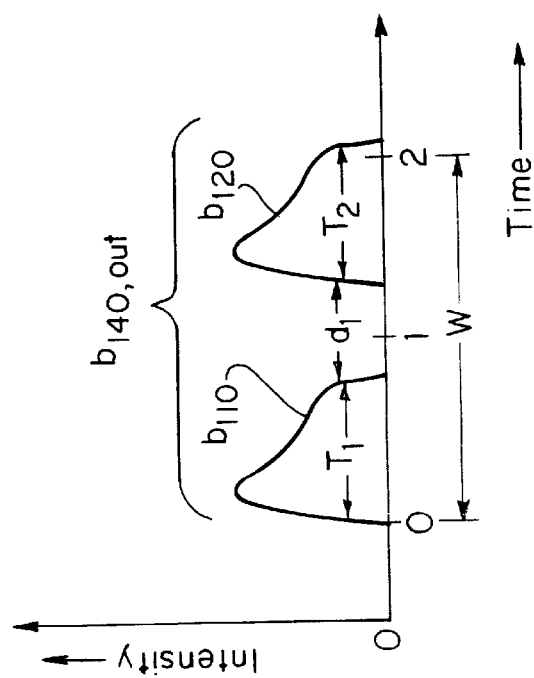
FIG. 2 is a graph of output beam intensity as a function of time for the first embodiment dye laser device of FIG. 1.

As illustrated in FIG. 2, the merged and output beams $b_{140,out}$ comprise two light pulses $b_{110}$, $b_{120}$ which are attributable respectively to the lasers 110, 120. As a result, the effective pulse width W generated by the first embodiment system 100 exceeds 2 msec even though the maximum obtainable pulse width from currently available dye lasers does not exceed 0.8 msec, and is closer to 0.5 msec for those available commercially. More specifically, the effective pulse width of the merged beam $b_{140}$ is equal to the pulse widths of the two pulsed laser beams $T_1$ plus $T_2$ in addition to an inter-pulse delay $d_1$. It should also be recognized that the time period $T_1$ plus $d_1$ corresponds to the time delay between the trigger signals $Sync_{110}$ and $Sync_{120}$ on the assumption that the lasers 110, 120 have the same latency to beam generation. As a result, the first embodiment enables the production of longer effective laser pulses. This feature enables the more effective treatment of thicker vascular lesions associated with, for example, portwine stains in adults in which the lower limit optimum pulse duration is about one millisecond long to treat vessels 100 microns or larger in diameter, as is. characteristic of this age group. Consequently, the thermal diffusion time of the target tissue, in this case, benign cutaneous vascular lesions, can be more accurately matched to optimize treatment and minimize damage to surrounding tissue.

Figure 3:
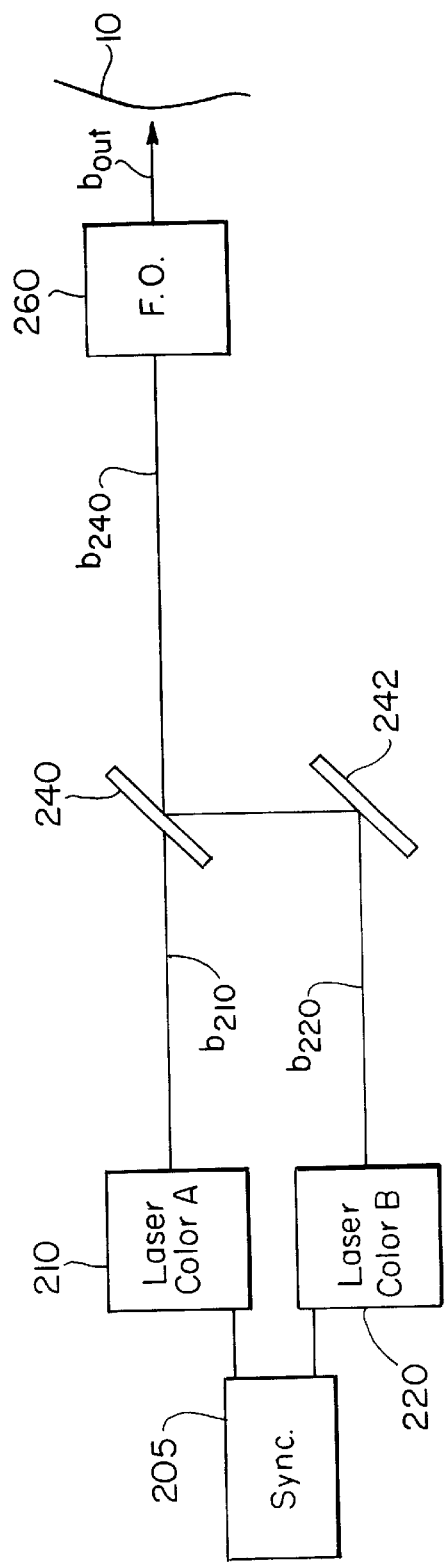
FIG. 3 is a schematic view of a second embodiment of a pulsed dye laser device of the present invention.

Referring to FIG. 3, a second embodiment 200 of the pulsed dye laser device is shown in which a combining network 240, 242 includes a dichroic mirror. As discussed in reference to FIGS. 1 and 2 in connection with the first embodiment 100, a synchronizer 205 generates two trigger signals to lasers 210 and 220. Since the trigger signal provided to laser 220 is delayed in time, pulse laser beam $b_{220}$ is delayed in time with respect to $b_{210}$. In contrast to the first embodiment 100, these laser beams $b_{210}$, $b_{220}$ are not orthogonally polarized but are comprised of different colored light. The combining network comprises a fold mirror 242 and a dichroic mirror 240. The fold mirror 242 redirects beam $b_{220}$ to converge spatially with beam $b_{210}$ at the dichroic mirror 240. This dichroic mirror 240 is constructed to transmit wavelengths characteristic of the beam $b_{210}$ but reflect light having a wavelength of beam $b_{220}$. As a result, a merged beam $b_{240}$ is generated which is comprised of a leading pulse resulting from the pulsed laser beam $b_{210}$ and a second delayed pulse which is resulting from the pulse $b_{220}$.

Ideally, the wavelengths or colors of the two pulsed beams $b_{210}$ and $b_{220}$ are optimized to maximize the wavelength dependent selectivity of the SP process. That is, in SP, the wavelength of the pulsed laser beam is selected to maximize the degree to which the beam is absorbed by the target tissue and minimize absorption in the surrounding tissue. These wavelengths are found in the range of 540–630 nm. The optimum wavelength, however, in many situations is dependent on the previous pulse. That is, the absorption spectra for hemoglobin becomes broader and more broadband as the hemoglobin is denatured due to preceding portions of the pulse. The color of merged beam $b_{240}$ is selected to dynamically match this change. The colors of the lasers 210, 220 can be formulated by selecting the appropriate dye recipe or intra-cavity treating elements such as etalons, bifringent filters, prisms or gradings. Thus, the present invention enables the achievement of higher levels of selectivity by matching the time dependent color of the merged pulse $b_{240}$ to the absorption characteristics as they change during the irradiation of the target tissue.

The first and second embodiments 100, 200 enable the generation of effective pulse lengths on the order of 200% greater than that achievable by single dye lasers. Cutaneous lesions comprising thicker walled ectatic vessels in some cases require even longer effective pulse lengths to optimize selectivity toward the target tissue. That is, effective pulse widths on the order of 2 msec, which are achievable as shown in FIG. 2, may still not be optimum. Many patients need energies greater than 100 millijoules with pulse durations of 1 to 10 msec. The third embodiment illustrated in FIG. 4 enables the combination of four pulse laser beams into a single output beam $b_{out}$. In this embodiment, a synchronizer 305 presents four trigger signals progressively delayed in time to four lasers 310, 314, 318, 320. As a result, four pulse laser beams $b_{310}$, $b_{314}$, $b_{318}$, $b_{320}$ are correspondingly generated.

The net spatial lateral distance between each of these beams is minimized by reflecting each of the outer beams $b_{310}$ and $b_{320}$ off a different pair of fold mirrors $f_1$ and $f_2$ in the case of beam $b_{310}$ and mirrors $f_3$ and $f_4$ in the case of beam $b_{320}$. All four laser pulse beams are then coupled into a single optical fiber 360 by focusing lens 342.

Preferably, the fiber 360 is large caliber between 0.4 and 1.5 mm and has a large acceptance numerical aperture of 0.3 to 0.42.

Figure 5:
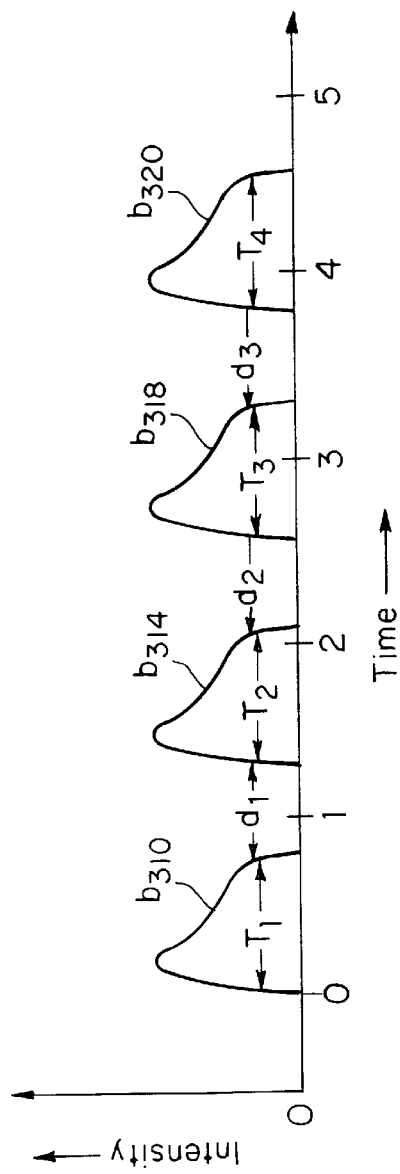
FIG. 5 is a graph of output beam intensity as a function of time for the third embodiment dye laser device of FIG. 4.

As illustrated in FIG. 5, the synchronizer 305 triggers each of these lasers 310, 314, 318, and 320 to generate the corresponding pulsed beams $b_{310}$, $b_{3/4}$, $b_{318}$, and $b_{320}$ to be evenly delayed in time so that the output beam bout will have an effective pulse width of approximately 4.5 msec.

Figure 4:
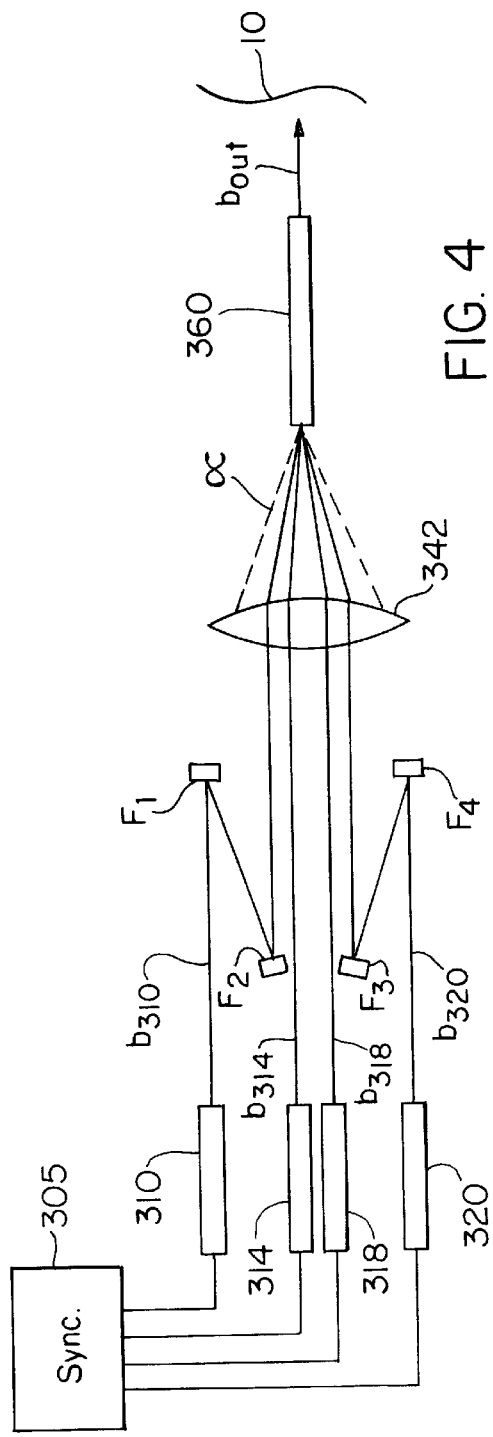
FIG. 4 is a schematic view of a third embodiment of the pulsed dye laser device of the present invention, combining the output of four lasers.

One potential modification of the third embodiment is to essentially connect fold mirrors $f_1$ and $f_4$ with an fold mirrors situated concentric to the main axis that would extend perpendicularly out of the page in FIG. 4 and be concentric with the lens 342. This change would enable a circular array of lasers to generate beams which could be coupled into the fiber optic cable 360 enabling even longer effective pulse widths.

Figure 6:
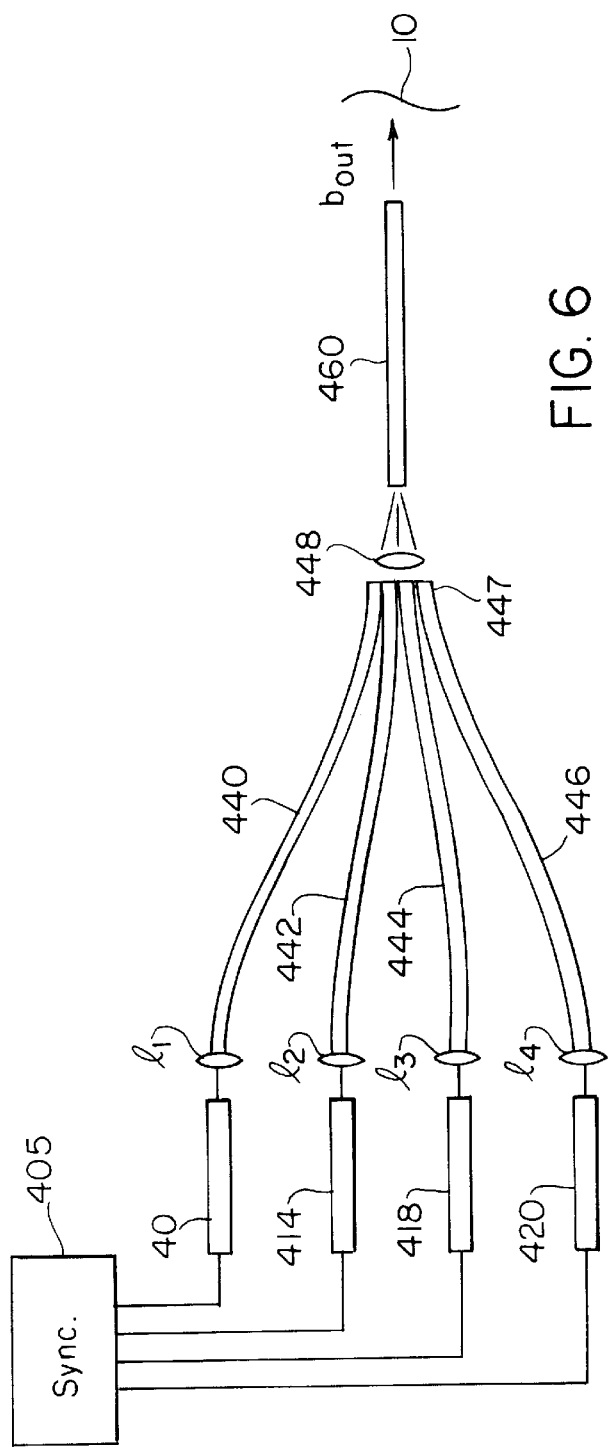
FIG. 6 is a schematic view of a fourth embodiment of the pulsed dye laser device of the present invention.

FIG. 6 shows a fourth embodiment of the present invention for also coupling the outputs of four lasers 410; 414, 418, 420 into a single optical fiber 460. In this embodiment, each of the lasers 410–420 is again controlled by a synchronizer 405 to successively generate in time the pulses. These pulses are individually coupled into separate fiber optic transfer cables 440, 442, 444, and 446 by focusing lens $1_1$–$1_4$. These transfer cables 440–446 are spatially brought together into essentially a single bundle of four parallel fibers at a proximal end 447. This enables a single lens 448 to couple the outputs of each of these fibers 440–446 into fiber 460 of the delivery system.

Figure 7:
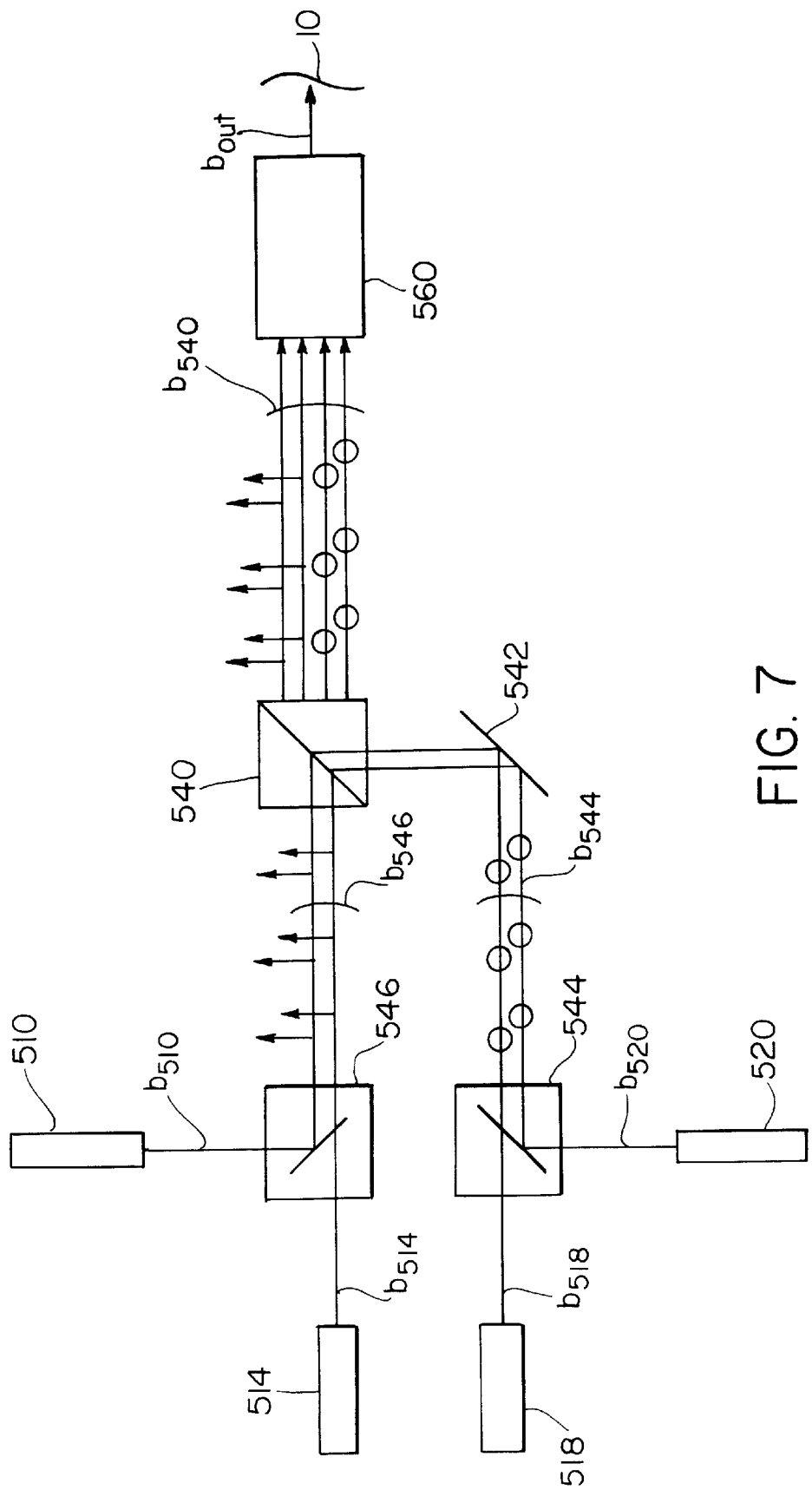
FIG. 7 is a schematic view of a fifth embodiment of the pulsed dye laser device of the present invention.

Finally, FIG. 7 shows a fifth embodiment of the present invention. This embodiment is somewhat related to a combination of the first and second embodiments of FIGS. 1 and 3 in that it incorporates both a polarizer 540 and dichroic mirrors 544, 546. But, this fifth embodiment couples the time delay outputs of a total of four lasers 510, 514, 518, and 520. More specifically, a first pair of lasers 518, 520 generate a pair of output beams $b_{518}$ and $b_{520}$ that have different colors but the same polarization. The dichroic mirror 546 is selected such that it reflects light having a color of beam $b_{510}$ but passes light having a color of beam $b_{514}$. As a result, the beams are spatially merged into a single beam $b_{546}$. In a similar vein, a second pair of lasers 518, 520 produce beams $b_{518}$ and $b_{520}$ that are merged into a single beam $b_{544}$ by dichroic mirror 544. Beams $b_{518}$ and $b_{520}$, however, have a polarization that is perpendicular to beams $b_{510}$ and $b_{514}$. A polarizer 540 merges beams $b_{544}$ and $b_{546}$ into single combined beam $b_{540}$, which is conveyed to the patient by optical fiber 560. This is accomplished by virtue of the fact that polarizer 540 is oriented such that light having the polarization of beam $b_{546}$ is transmitted but light having the orthogonal polarization of beam $b_{544}$ is reflected. Thus, a single beam $b_{540}$ is generated which comprises two colors and pulses from four lasers. It will be understood that the same outcome could be realized by reversing the configuration using two polarizers, and a single dichroic mirror, and rearranging the lasers 510–520.

While this invention has been particularly shown and describe with references to preferred embodiments thereof, it will be understood by those skilled in the art that various changes in form and details may be made therein without departing from the spirit and scope of the invention as defined by the appended claims.

What is claimed is:

1. A method for generating a long effective laser pulse for selective photothermolysis, therapy comprising:

generating multiple laser pulses;

generating a combined pulse from the multiple pulses, selecting a color of a subsequent one of the laser pulses in the combined pulse to maximize absorption in a target tissue of a patient in response to heating caused by a preceding one of the laser pulses in the combined laser pulse, the combined pulse having an effective pulse width greater than the laser pulses individually; and delivering the combined pulse to a patient through a delivery system.

\* \* \* \* \*